US006121010A

United States Patent [19]
Vallee et al.

[11] Patent Number: 6,121,010
[45] Date of Patent: Sep. 19, 2000

[54] METHODS AND ASSAYS USEFUL IN THE TREATMENT OF ALCOHOL DEPENDENCE OR ALCOHOL ABUSE

[75] Inventors: Bert L. Vallee, Boston; Wing-Ming Keung, Wayland, both of Mass.

[73] Assignee: The Endowment for Research in Human Biology, Boston, Mass.

[21] Appl. No.: 09/310,614

[22] Filed: May 12, 1999

Related U.S. Application Data

[60] Provisional application No. 60/085,148, May 12, 1998.
[51] Int. Cl.[7] .............................. C12Q 1/32; C12Q 1/26; A61K 31/405; A61K 31/135; A61K 31/35
[52] U.S. Cl. ............................. 435/26; 435/25; 514/415; 514/654; 514/456
[58] Field of Search ....................... 435/26, 25; 514/415, 514/654, 456

[56] References Cited

U.S. PATENT DOCUMENTS

| | | | |
|---|---|---|---|
| 5,204,369 | 4/1993 | Vallee et al. | 514/456 |
| 5,624,910 | 4/1997 | Vallee et al. | 514/27 |

FOREIGN PATENT DOCUMENTS

WO 93/00896  1/1993  WIPO.

OTHER PUBLICATIONS

Ambroziak et al., "Human Aldeyhyde Dehydrogenase," *J. Biol. Chem.*, 266(20):13011–13018 (1991).

Axelrod et al., "3–Methoxy–4–hydroxyphenylglycol sulfate, a new metabolite of epinephrine and norepinephrine," *Biochim. Biophys. Acta.*, 36:576–577 (1959).

Beaufay et al., "Intracellular Distribution of Some Dehydrogenase and Iron in Rat–Liver Tissue," *J. Cell Biol.*, 73:623–628 (1959).

Dietrich et al., "Biogenic Amine–Aldehyde Condensation Products: . . . ," *Annu. Rev. Pharmacol. Toxicol.*, 20:55–80 (1980).

Erwin et al., "Brain Aldehyde Dehydrogenase," *J. Biol. chem.* 241(15):3533–3539 (1966).

Feldstein, "Effect of Ethanol on Neurohumoral Amine Metabolism," Chapter 4, *The Biology of Alcoholism*, eds. B. Kissin & H. Beleiter, Plenum Press, New York, pp. 127–159 (1971).

Heyman et al., "Daidzin Decreases Ethanol Consumption in Rats," *Alcohol. Clin. Exp. Res.*, 20(6):1083–1087 (1996).

Johnson and Lardy, "Isolation of Liver or Kidney Mitochondria," *Methods in Enzymology*, 10:94–101 (1967), reprinted in EXS 71, "Toward a Molecular Basis of Alcohol Use and Abuse".

Keung and Vallee, "Daidzin: A potent, selective inhibitor of human mitochondrial aldehyde dehydrogenase," *Proc. Natl. Acad. Sci. USA*, 90:1247–1251 (1993).

Keung and Vallee, "Daidzin and daidzein suppress free–choice ethanol intake by Syrian Golden hamsters," *Proc. Natl. Acad. Sci. USA*, 90:10008–10012 (1993).

Keung and Vallee, "Therapeutic lessons from traditional Oriental medicine to contemparay Occidental pharmacology," *Toward a Molecular Basis of Alcohol Use and Abuse*, pp. 371–381, eds. B. Jansson et al. (1994).

Keung et al., "Daidzin inhibits mitochondrial aldehyde dehydrogenase and suppresses ethanol intake of Syrian golden hamsters," *Proc. Natl. Acad. Sci. USA*, 94:1675–1679 (1997).

Keung and Vallee, "Daidzin and its antidipsotropic analogs inhibit serotonin and dopamine metabolism in isolated mitochondria," *Proc. Natl. Acad. Sci., USA*, 95:2198–2203 (1998).

Klyosov et al., "Possible Role of Liver Cytosolic and Mitochondrial Aldehyde Dehydrogenases in Acetaldehyde Metabolism," *Biochemistry*, 35:4445–4456 (1996).

Koob et al., "Alcohol, the reward system and dependence," *Toward a Molecular Basis of Alcohol Use and Abuse*, ed. Jansson et al., pp. 103–114 (1994).

Lawrin et al., "Identification and Testing of New Drugs for Modulating Alcohol Consumption," *Psychopharmacology Bulletin*, 22(3):1020–1025 (1986).

Lin et al., "Isoflavonoid Compounds Extracted from *Pueraria lobata* Suppress Alcohol Preference in a Pharmacogenetic Rat Model of Alcoholism," *Alcohol. Clin. Exp. Res.*, 20(4):659–663 (1996).

Liskow and Goodwin, "Pharmacological Treatment of Alcohol Intoxication, Withdrawal and Dependence: A Critical Review," *J. Studies of Alcohol*, 48(4):356–370 (1987).

Overstreet et al., "Selective Alcohol Intake–Suppressant Effects of the Isoflavones Daidzin, Daidzein & Puerarin in Alcohol–Preferring FH Rats," *RSA/ISBRA Abstracts*, p. 16A, No. 76, (1996).

Overstreet et al., "Suppression of Alcohol Intake after Administration of the Chinese Herbal Medicine, NPI–028, and Its Derivatives," *Alcohol. Clin. Exp. Res.*, 20(2):221–227 (1996).

Peachey and Naranjo, "The Role of Drugs in the Treatment of Alcoholism," *Practical Therapeutics, Medical Progress*, pp. 45–59 (May 1985).

Rashkovetsky et al., "Human liver aldehyde dehydrogenases: new method of purification of the major mitochondrial and cytosolic enzymes . . . ," *Biochim. Biophys. Acta.*, 1205:301–307 (1994).

Tank et al., "Enzymology and Subcellular Localization of Aldehyde Oxidation in Rat Liver," *Biochm. Pharm.*, 30(24):3265–3275 (1981).

"Research on Promising Pharmacotherapies for Alcoholism," Program Announcement, Dept. of Health and Human Services (Catalog of Federal Domestic Assistance No. 13.273) pp. 1–17 (1990).

*Primary Examiner*—William R. A. Jarvis
*Attorney, Agent, or Firm*—Banner & Witcoff, Ltd.

[57]  ABSTRACT

A method for the treatment of alcohol abuse using daidzin and compounds analogous to daidzin is disclosed. Also disclosed is a method for screening compounds having antidipsotropic activity.

6 Claims, 3 Drawing Sheets

METHODS AND ASSAYS USEFUL IN THE TREATMENT OF ALCOHOL DEPENDENCE OR ALCOHOL ABUSE

STATEMENT OF RELATED APPLICATIONS

This application claims priority to U.S. Provisional Application Ser. No. 60/085,148 filed May 12, 1998, hereby incorporated by reference in its entirety.

BACKGROUND OF THE INVENTION

1. Field of the Invention

Embodiments of the present invention relate in general to novel methods useful in the treatment of alcohol dependence or alcohol abuse. Embodiments of the present invention also relate to novel assay systems useful in initial screening of compounds having an antidipsotropic effect. Such compounds are useful in therapeutic methods of reducing alcohol consumption as a treatment for alcohol dependence or alcohol abuse.

2. Description of Related Art

Alcohol abuse and alcohol dependence (i.e., alcoholism) are serious public health problems of modern society. In the United States alone, an estimated 13 million adults exhibit symptoms of alcohol dependence due to excessive alcohol intake, and an additional 7 million abuse alcohol without showing symptoms of dependence according to U.S. Government projections from studies conducted in the mid-1980s. Alcohol dependence and abuse are very expensive: in economic and medical terms, it will cost the U.S. well over $200 billion in 1991 with no prospect of falling or leveling off. The social and psychological damages inflicted on individuals as a consequence of alcohol abuse, e.g., children born with fetal alcohol syndrome (FAS) and victims of alcohol-related accidental death, homicide, suicide, etc., are immense.

While it is generally accepted that alcoholism and alcohol abuse are afflictions with staggering international economic, social, medical, and psychological repercussions, success in preventing or otherwise ameliorating the consequences of these problems has been an elusive goal. Only very recently the public view that alcoholism and alcohol abuse are remediable solely by moral imperatives has been changed to include an awareness of alcoholism and alcohol abuse as physiological aberrations whose etiology may be understood and for which therapy may be found through scientific pursuits. Both alcohol abuse and dependence arise as a result of different, complex, and as yet incompletely understood processes. At present, alcohol research is in the mainstream of scientific efforts.

Our studies on alcohol (ethanol or ethyl alcohol) have been based on the hypothesis that its abuse can ultimately be understood and dealt with at the molecular level. Such a molecular understanding, if achieved, would provide a basis for the identification and development of appropriate therapeutic agents, as well as assay systems useful in screening compounds as antidipsotropic agents.

Daidzin is the major active principle in extracts of Radix puerariae, a traditional Chinese medication that suppresses the ethanol intake of Syrian golden hamsters. See Keung, W. M. and Vallee, B. L. (1993) *Proc. Natl. Acad. Sci. USA* 90, 10008–10012 and Keung, W. M., Klyosov, A. A., and Vallee, B. L. (1997) *Proc. Natl. Acad. Sci. USA* 94, 1675–1679 each hereby incorporated by reference in its entirety for all purposes. It is the first isoflavone recognized to have this effect and to be useful in therapeutic methods of reducing alcohol consumption. See U.S. Pat. No. 5,624,910 hereby incorporate hereby incorporated by reference in its entirety for all purposes. Daidzin is also a potent and selective inhibitor of human mitochondrial aldehyde dehydrogenase (ALDH-2 also known as ALDH-I) which is an enzyme involved in the major enzymatic pathway responsible for ethanol metabolism in humans. See Keung, W. M. & Vallee, B. L. (1993) *Proc. Natl. Acad. Sci. USA* 90:1247–1251. See also, U.S. Pat. No. 5,204,369 hereby incorporated by reference in its entirety for all purposes.

The ethanol intake suppressive activity ("antidipsotropic activity") of daidzin has also been confirmed in Wistar rats, Fawn hooded rats, and the genetically bred P rats under various experimental conditions, including two-lever choice (ethanol/starch), two-bottle free-choice (ethanol/water), limited access, and ethanol deprived paradigms. See Keung, W. M. & Vallee, B. L. (1994) *EXS* 71, 1254–1260; Heyman, G. M., Keung, W. M. & Vallee, B. L. (1996) *Alcohol. Clin. Exp. Res.* 20, 1083–1087; Overstreet, D. H., Lee, Y. W., Rezvani, A. H., Pei, Y. H., Criswell, H. E. & Janowsky, D. S. (1996) *Alcohol. Clin. Exp. Res.* 20, 221–227; Overstreet, D. H., Rezvani, A. H. & Lee, Y. W. (1996) *Alcohol. Clin. Exp. Res.* 20 16A; Lin, R. C., Guthrie, S., Xie, C.-Y., Mai, K., Lee, D. Y., Lumeng, L. & Li, T.-K. (1996) *Alcohol. Clin. Exp. Res.* 20, 659–663. These laboratory findings identify or confirm daidzin or one or more of its derivatives, analogs and/or metabolites as important compounds in the treatment of alcohol abuse and/or alcoholism.

It has been postulated that the accumulation of biogenic amines, such as serotonin and dopamine, coupled with the inhibition of the enzyme aldehyde dehydrogenase (ALDH) leads to an accumulation of biologically active biogenic aldehydes or active condensation products of biogenic amines and aldehydes, such as tetrahydroisoquinolines and beta carbolines, and that these products may affect drinking behavior. See Dietrich, R. A. and Erwin, V. (1980) *Annu. Rev. Pharmacol. Toxicol.* 20, 55–80. In addition, studies have been suggested to identify pharmacological agents that may depress the desire to drink by directly interfering with the neurotransmitters serotonin, dopamine, and γ-aminobutyric acid (GABA) such as serotonin reuptake inhibitors, dopamine agonists, GABA receptor agonists, and narcotic antagonists. Numerous serotonin reuptake inhibitors, such as zimelidine, citalpram, viqualine, and fluvoxamine, are asserted to be effective in reducing alcohol consumption in animals. See Lawrin, M. O., Naranjo, C. A., and Sellers, E. M. (1986) *Psychopharmacology Bulletin* 22, 1020–1025. These compounds, however, react directly with the neurotransmitter.

It has also been postulated that ALDH-2 is somehow involved in the oxidation of aldehydes that derive from biologically active monoamines such as serotonin and dopamine in mammalian brain tissue via the action of monoamine oxidase. Axelrod, J., Kopin, I. J., and Mann, J. D. (1959) *Biochim. Biophys. Acta.* 36, 576–585 and Erwin, V. G. and Deitrich, R. A. (1966) *J. Biol. Chem.* 241, 3533–3539. Studies on dopamine metabolism in isolated mitochondria and various subcellular fractions identified ALDH-2 as the principal enzyme that catalyzes the oxidation of dopamine derived 3,4-dihydroxyphenylacetaldehyde (DOPAL) in rat liver. Tank, A. W., Weiner, H. And Thurman, J. A. (1981) *Biochem. Pharmacol.* 30, 3265–3275. Recent kinetic analyses have shown that both DOPAL and serotonin-derived 5-hydroxyindole-3-acetaldehyde (5-HIAL) are substrates for ALDH-2. Ambroziak, W. And Pietruszko, R. (1991) *J. Biol. Chem.* 266, 13011–13018.

However, the art has not recognized whether isoflavone based compounds such as daidzin or daidzin analogs are capable of interacting with the enzyme systems of neurotransmitters or how such compounds would even come in contact with such enzyme systems given the nature and structure of the isoflavone based compounds. As such, the art provides no guidance as to whether isoflavone based compounds are chemically capable of interacting with the neurotransmitter enzyme systems, such as where crossing of the blood-brain barrier may be necessary or are capable of having any effect on neurotransmitter enzyme systems, especially in a manner to reduce alcohol consumption or otherwise affect the concentration or efficacy of substrates within the enzyme system that regulate ethanol drinking behavior. A complete understanding of whether daidzin interacts with neurotransmitter enzyme systems to suppress ethanol intake is, therefore, necessary and beneficial. Such a further and complete understanding of the mechanism of action of daidzin's antidipsotropic activity and its interaction with neurotransmitter enzyme systems will identify other compounds useful as antidipsotropic agents, as well as provide novel assay systems to screen compounds for antidipsotropic activity.

SUMMARY OF THE INVENTION

Embodiments of the present invention are based on the discovery that the enzyme systems of certain biologically active monoamines, such as serotonin (5-HT) and dopamine (DA) in mammalian tissue, can be inhibited using daidzin or analogous compounds and that the inhibition alters the concentration of substrates that regulate ethanol drinking behavior. More particularly, embodiments of the present invention are directed to inhibiting the oxidation of aldehydes that derive from neurotransmitters such as serotonin and dopamine via monoamine oxidase (MAO). It has been discovered that daidzin and daidzin analogs are effective in increasing the concentration of aldehydes formed during the catabolism of certain neurotransmitters and that the increase in aldehyde concentration attributable to the neurotransmitter enzyme systems is effective in reducing alcohol consumption. Further embodiments of the present invention are directed to novel assay systems based on the neurotransmitter enzyme systems which may be used to screen compounds for their ability to inhibit the formation of certain acid products or raise the concentration of certain aldehyde products as a measure of a candidate compound's ability to reduce alcohol consumption in a mammal including a human. The assays of the present invention based upon the monoamine enzyme systems for serotonin and dopamine provide for the first time a reliable system for quantitatively predicting antidipsotropic activity of candidate compounds as a function of aldehyde accumulation.

The present invention additionally provides daidzin analogs which are capable of inhibiting the enzyme systems of certain neurotransmitters. The invention encompasses compounds of the formula I:

wherein:
R represents
straight chain alkyl having 1–11 carbon atoms, or branched chain alkyl having 1–30 carbon atoms, where the branched chain alkyl comprises a straight chain alkyl portion having 1–11 carbon atoms substituted with straight or branched chain lower alkyl groups having 1–6 carbon atoms;

hydroxyalkyl where the alkyl portion is straight chain alkyl having 2–11 carbon atoms, or branched chain alkyl having 2–30 carbon atoms, where the branched chain alkyl comprises a straight chain alkyl portion having 2–11 carbon atoms substituted with straight or branched chain lower alkyl groups having 1–6 carbon atoms;

aminoalkyl where the alkyl portion is straight chain alkyl having 2–11 carbon atoms, or branched chain alkyl having 2–30 carbon atoms, where the branched chain alkyl comprises a straight chain alkyl portion having 2–11 carbon atoms substituted with straight or branched chain lower alkyl groups having 1–6 carbon atoms;

carboxyalkyl where the alkyl portion is straight chain alkyl having 2–11 carbon atoms, or branched chain alkyl having 2–30 carbon atoms, where the branched chain alkyl comprises a straight chain alkyl portion having 2–11 carbon atoms substituted with straight or branched chain lower alkyl groups having 1–6 carbon atoms; or where X is straight chain alkylene having 2–11 carbon atoms, or branched chain alkylene having 2–30 carbon atoms, where the branched chain alkylene comprise a straight chain alkylene portion having 2–11 carbon atoms substituted with straight or branched chain lower alkyl groups having 1–6 carbon atoms; and R' is straight or branched alkyl having 1–6 carbon atoms.

The invention also encompasses compounds of the formula:

wherein
R represents straight or branched chain alkyl having 1–11 carbon atoms;
hydroxyalkyl where the alkyl portion is straight or branched alkyl having 2–11 carbon atoms;
carboxyalkyl where the alkyl portion is straight or branched alkyl having 2–11 carbon atoms; or where
X is straight or branched chain alkylene having 2–11 carbon atoms; and R' is straight or branched alkyl having 1–6 carbon atoms.

By lower alkyl in the present invention is meant straight or branched chain alkyl groups having 1–6 carbon atoms, such as, for example, methyl, ethyl, propyl, isopropyl, n-butyl, isobutyl, tert-butyl, pentyl, 2-pentyl, isopentyl, neopentyl, hexyl, 2-hexyl, 3-hexyl, and 3-methylpentyl, By alkyl in the present invention is meant (i) straight chain alkyl groups having 1–11 carbon atoms, such as, for example, methyl, ethyl, propyl, n-butyl, pentyl, hexyl, heptyl, octyl, nonyl, decyl, and undecyl, or (ii) branched chain alkyl groups having 1–30 carbon atoms comprising a straight chain alkyl portion having 1–11 carbon atoms substituted with straight or branched chain lower alkyl groups having 1–6 carbon atoms. Examples of such branched chain alkyl groups are 4-n-butyl-undecane, 5-ethylnonane, 4-ethyl-5-isobutyl-5-methyldecane, 3-propyl-4-ethyloctane, and 4-isooctyl-3-propylundecane.

By hydroxyalkyl is meant an alkyl group substituted with a hydroxy moiety at any available position of the alkyl group. Representative hydroxyalkyl groups are, for example, hydroxyethyl, hydroxymethyl, hydroxyhexyl, hydroxypentyl, and hydroxydecyl. In addition, the alkyl groups may be substituted with more than one hydroxy moiety, i.e., the hydroxyalkyl may be a polyhydroxyalkyl group.

By carboxyalkyl is meant substituents of the structure:

$$HO_2C-Y-$$

where Y represents straight or branched chain alkylene having 1–11 carbon atoms.

In addition the alkyl groups may be substituted with more than one carboxy moiety, i.e., the carboxyalkyl may be a polycarboxyalkyl group.

Furthermore, the alkyl groups may be substituted with one or more hydroxy substituents and one or more carboxy substituents. The hydroxy and carboxy substituents may also be esterified using, respectively, short chain (1–6 carbon atoms) acids and alcohols.

The compounds derived from daidzein are named as ethers of the 7-hydroxyl group of the aglycone daidzein; they resemble daidzin in that there is no free hydroxyl at the 7-position, but differ in that the daidzin glucosidic group is an acetal rather than an ether. The compounds can be routinely prepared by methods well known in the art such as reaction of daidzein with various ω-halo fatty acids, such as bromo or iodo, or with ethyl iodide.

The analogs of daidzin can be used in methods to inhibit the enzyme systems of serotonin and dopamine in a manner to increase concentrations of aldehydes present in the enzyme system or inhibit the formation of corresponding acids present in the enzyme system. Such daidzin analogs are potent and have similar significant in vivo effects on alcohol consumption in animal models. Thus, the daidzin and daidzin analogs are useful in methods of reducing alcohol consumption by inhibiting the enzyme systems of certain monoamines, such as serotonin and dopamine in a manner to increase aldehyde concentrations resulting from the catabolism of the neurotransmitters. In addition, novel assay systems are provided according to the present invention whereby candidate compounds can be screened for their ability to effect the enzyme systems of serotonin or dopamine. It has been discovered that compounds which raise aldehyde concentrations within the serotonin or dopamine enzyme systems are also effective as antidipsotropic agents, i.e. agents which reduce alcohol consumption. According to the present invention, a novel assay system is provided whereby a candidate compound is contacted with a monoamine enzyme system, such as a serotonin or dopamine enzyme system. The novel assay system quantitatively gauges the ability of a candidate compound to reduce alcohol consumption based upon its ability to raise aldehyde concentrations within the serotonin or dopamine enzyme systems. The novel assay systems of the present invention, therefore, avoid unnecessary in vivo screening to determine antidipsotropic activity.

BRIEF DESCRIPTION OF THE DRAWINGS

In the course of the detailed description of certain preferred embodiments to follow, reference will be made to the attached drawings, in which.

DETAILED DESCRIPTION OF CERTAIN PREFERRED EMBODIMENTS

Embodiments of the present invention relate to inhibitors of aldehyde dehydrogenase present in the enzyme system in humans that is responsible for conversion of aldehyde to carboxylic acid in the metabolic pathways for the neurotransmitters serotonin or dopamine. Embodiments of the present invention are further directed to synthetic inhibitory compounds having an isoflavone structure and analogous to daidzin. Still further embodiments of the present invention are directed to novel assays based upon the enzyme systems of serotonin and dopamine useful for screening compounds having antidipsotropic activity.

In particular, daidzin and daidzin analogs of formula I have been unexpectedly found to be direct, potent yet selective and reversible inhibitors of ALDH-2 which catalyzes the conversion of aldehyde to carboxylic acid in the following enzyme systems for serotonin and dopamine.

EXAMPLE I

Compounds

Daidzin and structurally related compounds were either commercially available or prepared according to standard techniques. See U.S. Pat. No. 5,624,910 previously incorporated by reference in its entirety. Daidzin analogs within the scope of the present invention not only include the compounds represented by formula I but also those wherein the glucose is replaced with a different sugar moiety. For example, L and D aldo- or keto-tetroses, pentoses, hexoses, heptoses or the amino, alcohol and/or acid derivatives of such tetroses, pentoses, hexoses or heptoses; or wherein the glucose is replaced by the deoxy analogs of such tetroses, pentoses, hexoses or heptoses. Alternatively, the glucose (GlcO) moiety of daidzin may be replaced by alkoxy or acyloxy groups at the 7-position bearing various chain lengths, for example, up to 11 or more, comprising any of straight chain alkyl, peptidic, polyether, etc. backbones, and the backbones may be substituted with various neutral (e.g., hydroxyl, sugar, etc.) or charged (e.g., carboxylate, phosphate, phosphonate, sulfate, sulfonate, etc.) moieties. Additionally suitable moieties (e.g., carboxylate, hydroxyl, etc.) may be esterified.

7-ω-carboxyalkyl ethers of daidzein were prepared as follows. Daidzein (10 mmoles) was suspended in 40 ml of acetone, 10 ml of 2 N KOH was added, followed by 10 mmoles of solid ω-bromohexanoic acid, ω-bromoheptanoic acid, ω-bromoundecanoic acid or ethyl iodide. The mixture was stirred under reflux for 3 days. The potassium salt of the 7-(ω-carboxyalkyl) ether of daidzein was recovered by filtration, washed with acetone and dried; yield, 20–35%.

The following 7-O-substituted daidzein derivatives, namely, 7-O-(6-bromohexyl)-daidzein, 7-O-(triethyl-6-aminohexyl)-daidzein, 7-O-(triethyl-6-aminoethyl)-daidzein, 7-O-(6-aminohexyl)-daidzein, 7-O-daidzein-6-bromoheptanoate, 7-O-daidzein-2-chloroacetate, 7-O-daidzein-2-bromoacetate, and 7-O-daidzein-3-dimethylaminopropionate, were synthesized as follows.

7-O-(6-bromohexyl)-daidzein was prepared by refluxing 1.25 g daidzein, 12.2 g 1,6-dibromohexane, and 2.5 ml 11.2% KOH in 25 ml acetone overnight. The reaction mixture was extracted into petroleum ether from water, dried and crystallized from chloroform.

7-O-(triethyl-6-aminohexyl)-daidzein was prepared by refluxing 3 mmol 7-O-(6-bromohexyl)-daidzein with 4 ml triethylamine in 10 ml dimethylformamide (DMF) for 8 hours. The reaction mixture was evaporated to dryness and the product was extracted with water.

7-O-(triethyl-6-aminoethyl)-daidzein was synthesized by refluxing 10 g daidzein, 20 ml 2 N KOH, and 8.5 ml 1,2-dibromoethane in 200 ml acetone for 12 hours. The reaction mixture was dried, redissolved in 150 ml chloroform, and filtered to remove daidzein. Solvent was evaporated and the product, 7-O-(2-bromoethyl)-daidzein, was recrystallized from hexane. 7-O-(2-bromoethyl)-daidzein was then refluxed with 4 ml triethylamine in 10 ml DMF for 8 hours. The reaction mixture was evaporated to dryness and product was extracted with water. 7-O-(6-aminohexyl)-daidzein was made by saturating a mixture of 50 mg 7-O-(6-bromohexyl)-daidzein, 5 ml DMF, and 15 ml ethanol with gaseous ammonia for 24 hours. The reaction mixture was evaporated and the final product was recrystallized from water.

The 7-O-daidzein esters of 6-bromoheptanoic acid (7-O-daidzein-6-bromoheptanoate), chloroacetic acid (7-O-daidzein-2-chloroacetate), bromoacetic acid (7-O-daidzein-2-bromoacetate), and 3-dimethylaminopropionic acid (7-O-daidzein-3-dimethylaminopropionate) were prepared by adding the respective acids (10 mmol) and dicyclohexylcarbodiimide (10 mmol) to a solution of daidzein (10 mmol) in 20 ml acetone. The solution was stirred overnight at 0° C. Solvents in the resulting mixtures were evaporated and final products were crystallized from chloroform.

These examples are not exhaustive in scope but suggest to those skilled in the art routes to the identification of daidzin derivatives (i.e., analogs) having increased bioavailability and improved potency, selectivity, controlled release, solubility, absorbability and/or stability.

EXAMPLE II

ALDH-Inhibitory Activity

ALDH activity of daidzin and daidzin analogs was assayed as previously described in U.S. Pat. No. 5,624,910 and Keung, W. M., Klyosov, A. A. & Vallee, B. L. (1997) Proc. Natl. Acad. Sci. USA 94, 1675–1679, such as by monitoring the increase in absorbance at 340 nm due to the formation of NADH ($\epsilon 340=6.22$ mM−1 cm−1) in a Varian Cary 219 spectrophotometer at pH 9.5 when acetaldehyde was used as the substrate, or by monitoring the increase in fluorescence at 430 nm on formation of 6-dimethylamino-2-naphthoic acid ($\lambda$ex=330 nm) in a Perkin-Elmer MPF3 spectrofluorimeter when 6-DMA-2-NA was used as the substrate. Human, hamster, and rat liver mitochondrial and cytosolic ALDH isozymes were purified as described in Klyosov, A. A., Rashkovetsky, L. G., Tahir, M. K. and Keung, W. M., (1996) *Biochemistry* 35, 4445–4456. Stock solutions of all water soluble substrates and test compounds were made in Milli-Q water and all others were in methanol. The final concentrations of methanol in the assay mixtures were ≦1% and had no effect on the activities of the ALDH isozymes. The kinetic parameters $K_m$ and $V_{max}$ for cytosolic ALDHs have been determined from Lineweaver-Burk plots derived from duplicate determinations of initial velocities whereas those for the mitochondrial isozymes were determined from progress kinetic curves in accordance with the teachings of Rashkovetsky, L. G., Maret, W. & Klyosov, A. A. (1994) *Biochim. Biophys. Acta* 1205, 301–307 hereby incorporated by reference in its entirety.

EXAMPLE III

Antidipsotropic Activity

The ethanol intake suppressive activity of daidzin and its structural analogs was determined using alcohol preferring Syrian golden hamsters as previously described. See Keung, W. M. & Vallee, B. L. (1993) *Proc. Natl. Acad. Sci. USA*, 90, 10008–10012.

EXAMPLE IV

Competitive ($K_i$) and Noncompetitive ($\alpha K_i$) Inhibition Constants of 7-O-Substituted Daidzein Derivatives with Human Mitochondrial ALDH

TABLE I

| No. | R- | ALDH-2 $K_i$ | $\alpha K_i$ | ETOH Intake Suppression, % |
|---|---|---|---|---|
| 1 | H- (daidzein) | 9.2 | 180 | 32 |
| 2 | Glc- (daidzin) | 0.042 | 0.65 | 64 |
| 3 | $HOOC(CH_2)_5$— | 0.009 | 0.15 | 70 |
| 4 | $HOOC(CH_2)_6$— | 0.009 | 0.14 | 69 |
| 5 | $HOOC(CH_2)_9$— | 0.004 | 0.05 | 84 |
| 6 | $HOOC(CH_2)_{10}$— | 0.003 | 0.04 | 86 |
| 7 | $CH_3CH_2$— | 0.035 | 0.56 | nd |
| 8 | 1,3-dioxane-ethyl- | | | 32 |
| 9 | $Br(CH_2)_4$— | | | 29 |
| 10 | $Br(CH_2)_6$— | 0.003 | 0.07 | 14 |
| 11 | $(CH_3CH_2)_3N^+(CH_2)_6$— | 0.005 | 0.08 | nd |
| 12 | $NH_2(CH_2)_4$— | | | 18 |
| 13 | $NH_2(CH_2)_6$— | 0.036 | 0.60 | nd |
| 14 | $Br(CH_2)_6CO$— | 0.02 | 0.26 | nd |
| 15 | $(CH_3CH_2)_3N^+(CH_2)_2$— | 0.08 | 1.6 | nd |
| 16 | $ClCH_2CO$— | 1.06 | 10.6 | nd |
| 17 | $BrCH_2CO$— | 1.8 | 20 | nd |
| 18 | $(CH_3)_2N(CH_2)_3CO$— | 1.75 | 24 | nd |
| 19 | $HOCH_2(OH)CHCH_2$— | | | 17 |
| 20 | Puerarine | 15 | 440 | 0 |
| 21 | Chrysin | 35 | 110 | 0 |
| 22 | 7,8-Dihydroxyflavone | 35 | 270 | 0 |

As indicated in Table I above, all of the 7-O-substituted daidzein derivatives are better ALDH-2 inhibitors than is daidzein, and four of them (compounds #3 to #6) are even better than daidzin. The 7-O-(6-bromohexyl)- and 7-O-(6-triethylaminohexyl)-daidzein (compounds #10 and #11 respectively) are extremely potent inhibitors of human ALDH-2 with $K_i$ values of 3 and 5 nM, respectively. The 6-bromoheptanoate of daidzein (compound #14) is less potent than 7-O-(6-bromohexyl)-daidzein. The 7-O-daidzein esters of short chain acids, e.g. 2-chloroacetic acid, 2-bromoacetic acid, and 3-dimethylaminopropionic acid, (compounds #16, #17, and #18, respectively) are less potent inhibitors relative to daidzin. As indicated by the data in Table 1, the long chain 7-O-(ω-carboxyalkyl)- derivatives of daidzein are the most potent inhibitors of ALDH-2 (compounds #3 to #6).

EXAMPLE V

Antidipsotropic Activity of 7-O-substituted Daidzeins

The antidipsotropic effect of two of the strongest (7-O-[ω-carboxypentyl]- and 7-O-[ω-carboxyhexyl]-daidzein) and three of the weakest (puerarin, chrysin, and 7,8-dihydroxyflavone) ALDH-2 inhibitors were tested in ethanol-preferring golden hamsters and the results reported in Table I above. Daidzin and daidzein were also tested at equivalent doses for comparison. An i.p. dose of daidzin or daidzein (70 meq/hamster/day) suppresses hamster ethanol intake by 64% or 32%. At equivalent doses, puerarin, chrysin and 7,8-dihydroxyflavone do not exert any significant effect on ethanol intake whereas the two 7-O-(ω-carboxyalkyl)-daidzeins are somewhat better than daidzin (about 70% suppression).

EXAMPLE VI

Mitochondria-Catalyzed Monoamine Metabolism Using 5-HT and DA as the Substrates According to the teachings of the present invention, a method of screening compounds for antidipsotropic activity is provided. A test compound is selected, for example, based upon the teachings herein with respect to the structure of daidzin or daidzin analogs known to have antidipsotropic activity. However it is to be understood that any compound can be selected for assay according to the teachings of the present invention, as the purpose of the assay is to identify or screen compounds having antidipsotropic activity. The present invention is therefore not limited to compounds structurally analogous to daidzin.

A mitochondrial or other preparation including serotonin, monoamine oxidase and aldehyde dehydrogenase is then provided under conditions sufficient for the monoamine oxidase to convert serotonin to 5-hydroxyindole-3-acetaldehyde and for the aldehyde dehydrogenase to convert the 5-hydroxyindole-3-acetaldehyde to 5-hydroxyindole-3-acetic acid. It is to be understood that assays based upon the enzyme system for dopamine are also useful in the practice of the present invention. For example a mitochondrial or other preparation including dopamine, monoamine oxidase and aldehyde dehydrogenase can be provided under conditions sufficient for the monoamine oxidase to convert dopamine to 3,4-dihydroxyphenyl-3-acetaldehyde and for the aldehyde dehydrogenase to convert the 3,4-dihydroxyphenyl-3-acetaldehyde to 3,4-dihydroxyphenylacetic acid. For purposes of simplicity of explanation, however, the following discussion will only reference a serotonin-based assay.

The 5-hydroxyindole-3-acetaldehyde can then be measured outside of the presence of a test compound. Optionally, the 5-hydroxyindole-3-acetic acid formed can also be measured. Individual assays can be conducted with known compounds having antidipsotropic activity, including daidzin and daidzin analogs to obtain additional measurements of the amounts of 5-hydroxyindole-3-acetaldehyde produced in the presence of each known compound thereby creating a database of values corresponding to known antidipsotropic compounds where the compound's ability to suppress or reduce ethanol consumption has previously been determined. A comparison can then be made between the compound's ability to reduce ethanol intake (i.e. % ethanol intake suppression) and the amount of 5-hydroxyindole-3- acetaldehyde produced by a mitochondrial preparation including the compound. In this manner, antidipsotropic activity can be described as a function of the amount of 5-hydroxyindole-3-acetaldehyde produced by a mitochondrial preparation including the compound.

An additional mitochondrial preparation is then contacted with the test compound and the 5-hydroxyindole-3-acetaldehyde is then measured. Optionally, 5-hydroxyindole-3-acetic acid can also be measured. The amount of 5-hydroxyindole-3-acetaldehyde is then compared with the database including the amounts of 5-hydroxyindole-3-acetaldehyde formed in the presence of known compounds having antidipsotropic activity to determine the antidipsotropic potency of the test compound. According to the assay, compounds having the effect of increasing the amount of 5-hydroxyindole-3-acetaldehyde relative to an assay where no compound is present are predicted to have antidipsotropic activity.

Specifically, daidzin and daidzin analogs were tested to determine their effects on hamster ethanol intake and the aldehyde intermediate accumulation during mitochondria-catalyzed monoamine metabolism using 5-HT and DA as the substrates. Hamster liver mitochondrial preparations were obtained by the well-known method of Johnson & Lardy (see John, D. & Lardy, H. (1967) *Meth. Enzymol.* 10, 94). The integrity of these mitochondrial preparations, evaluated by measuring their latent glutamate dehydrogenase activity according to the methods of Beaufay, H., and Bendall, D. S., Baudhuin, P. & deDuve, C. (1959) *J. Cell Biol.* 73, 623–628 before and after the metabolic study, were over 97% and 93%, respectively.

5-HT and DA metabolism in the mitochondrial preparations were assayed by monitoring the formation of their respective metabolites 5-HIAL, 5-HIAA and DOPAL, DOPAC, and the depletion of DA and 5-HT, in a 0.5 ml standard pH 7.4 assay medium containing 10 mM Tris-HCl, 0.3 M mannitol, 2.5 mM $MgCl_2$, 10 mM $K_2HPO_4$, 10 mM KCl, 10 $\mu$M of substrate, 0, 0.09, 0.3, 0.9, 3, or 9 $\mu$M of daidzin or its structural analogs, and 40 $\mu$g (protein) of freshly prepared mitochondrial preparations. Reactions were initiated by the addition of mitochondria and allowed to proceed in a 37° C. shaking water bath for 30 min. Reactions were terminated by the addition of 0.05 ml each of ice-cold 1 M $HClO_4$ and 10 mM EDTA. The samples were kept on ice for 1 hour followed by centrifugation (12,000 rpm) in a microcentrifuge (Microspin 24S, Sorvall) for 15 min. DA, 5-HT, and their major metabolites in the supernatant were analyzed directly by HPLC.

The HPLC system used in this study consisted of a BAS Sample Sentinel Autosampler with refrigerated (4° C.) sample compartment, PM80 solvent delivery system, and a LC-26 on-line degasser. The detector is a LC-4C amperometric controller with a CC-5 cross-flow thin-layer (0.005") electrochemical cell composed of glassy carbon and silver/silver chloride reference electrode (Bioanlytical Systems, Inc., West Lafayette, Ind.). For routine analysis, the potential and sensitivity were set at 650 mV and 20 nA full scale, respectively. Column temperature was maintained with a Waters Temperature Control Module (Waters, Milford, Mass). DA and 5-HT were analyzed on a BAS phase II ODS-3, 3 $\mu$m, 3.2×100 mm column. The column was developed at 40° C. at 1 ml/min in a mobile phase that contained 1.23% monochloroacetic acid (Sigma), 0.02% sodium 1-octyl sulfate (Lancaster, Windham, N.H.), 0.025% $EDTA-Na_2$, and 5% acetonitrile (v/v), pH 3. The retention times for DA and 5-HT were 7.7 and 20.6 min, respectively. DOPAL, DOPAC, 5-HIAL and 5-HIAA were analyzed on a Beckman ultrasphere ODS-5, 5$\mu$, 4.6×250 mm column. The column was developed at 30° C. at 1 ml/min in a mobile phase containing 3% methanol (v/v), 2.5% acetonitrile (v/v), 0.1% TFA, 50 mM NaCl, and 0.2 mM EDTA. The retention times for these metabolites were 8.6, 14.3, 14.6 and 19.9 min, respectively. Data were collected and analyzed with a Nelson data collection system (Perkin-Elmer) or a Waters 740 Data Module. The effect of a test compound on 5-HIAL or DOPAL accumulation measured at five different concentrations were averaged and presented as % of control.

EXAMPLE VII

Comparison of Ethanol Intake Suppression vs. 5-HIAL Accumulation

Figure 1:
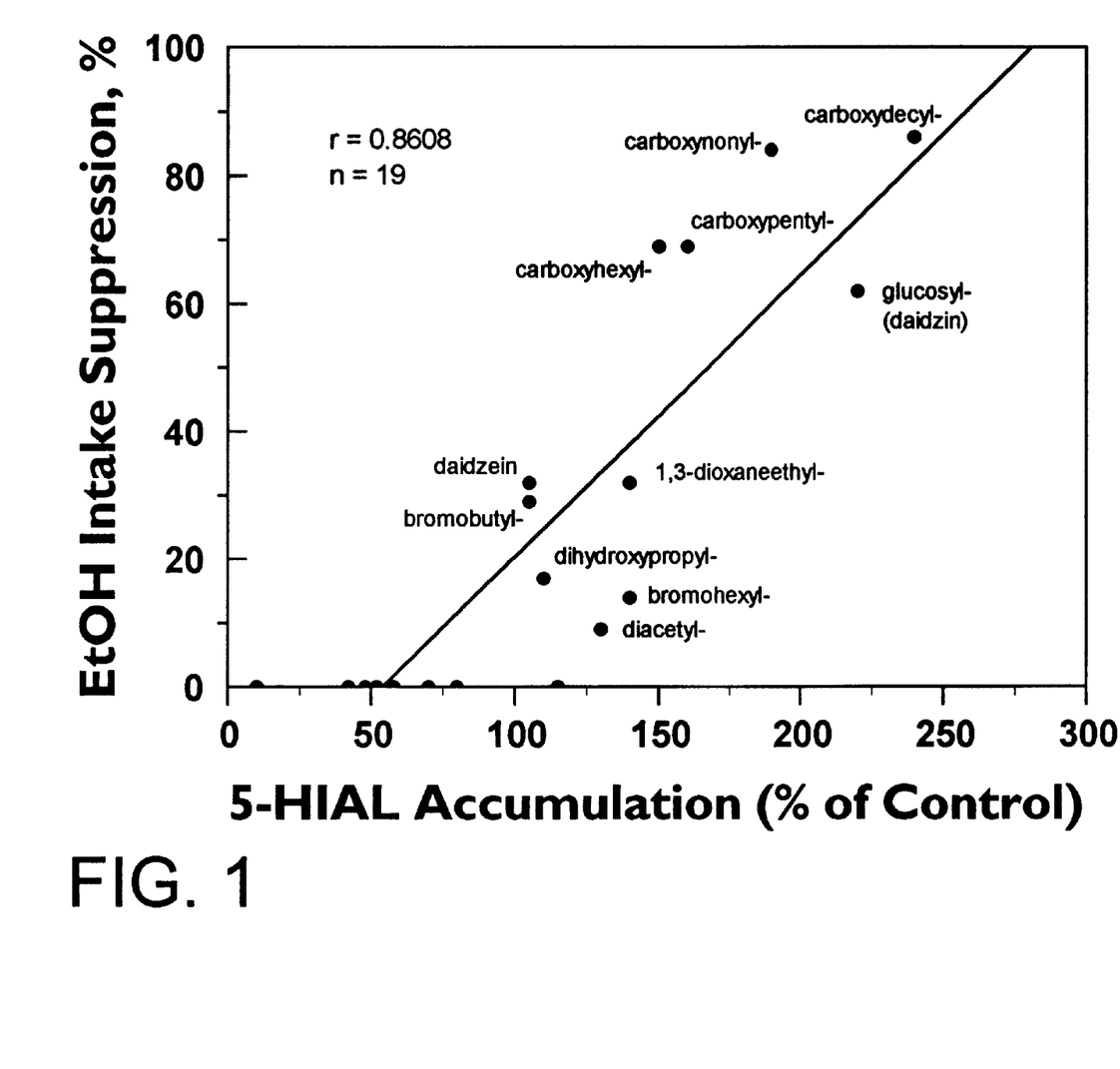
FIG. 1 is a graph of the percent ethanol intake suppression versus 5-HIAL accumulation aqs a percent of control.
Figure 2:
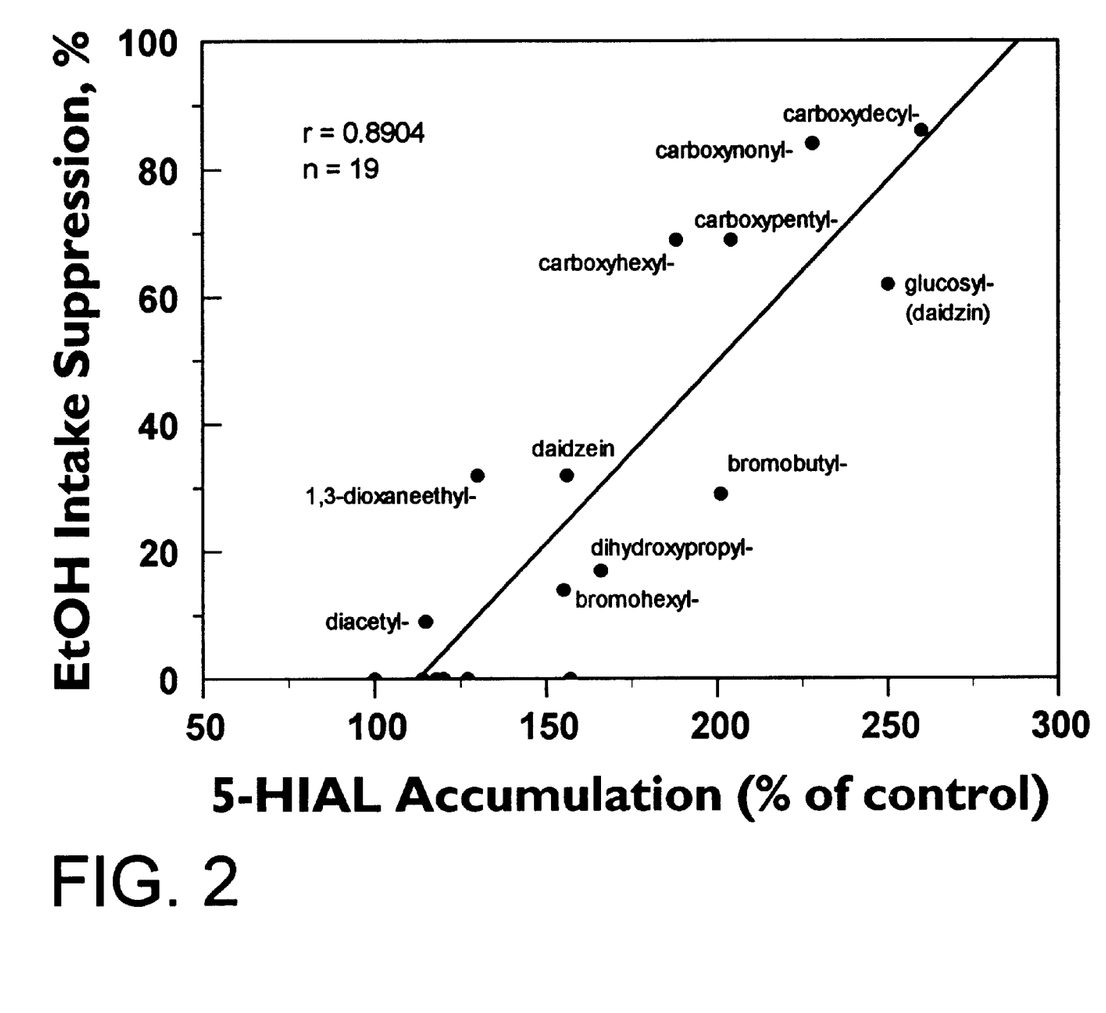
FIG. 2 is a graph of the percent ethanol intake suppression versus DOPAL accumulation aqs a percent of control.

The following compounds were tested for their antidipsotropic activity and ability to inhibit the enzyme system for serotonin: daidzin, daidzein, 7,8-dihydroxyflavone, genestein, 5,7-dihydroxyflavone, biochanin A and the following derivatives of daidzin: carboxydecyl, carboxynonyl, carboxypentyl, carboxyhexyl, bromobutyl, 1,3-dioxaneethyl, dihydroxypropyl, aminobutyl, bromohexyl, diacetyl, aminohexyl, allyl, ethyl and bromopropyl. The results of ethanol intake suppression plotted as a function of 5-HIAL accumulation are presented in FIG. 1. Among the compounds identified in FIG. 1, 11 of them suppressed hamster ethanol intake with long chain 7-ω-carboxyalkyl-derivatives and daidzin being most active (>60 suppression) followed by daidzein, 2-(1,3-dioxan-2-yl)ethyl-, 7-ω-bromobutyl-daidzein derivatives (~30% suppression). 7-ω-bromohexyl-, 7-ω-aminobutyl- and a 2,3-dihydroxypropyl-daidzein derivatives were only marginally active when tested at equivalent doses (0.07 meq/hamster/day). Nine of the 20 compounds tested did not suppress ethanol intake at equivalent dose tested. Those compounds were, genestein, 7,8-dihydroxyflavone, 5,7-dihydroxyflavone and the following derivatives of daidzin: aminohexyl, allyl, ethyl, and bromopropyl. Compounds that suppressed ethanol intake also induced 5-HIAL accumulation during mitochondria-catalyzed 5-HT metabolism: the more the 5-HIAL accumulation, the greater the ethanol intake suppression. Compounds that did not induce 5-HIAL accumulation did not suppress ethanol intake. FIG. 1 clearly demonstrates a positive correlation between ethanol intake suppression and 5-HIAL accumulation. As can be seen in FIG. 2, correlation was also observed when the mitochondrial MAO/ALDH pathway was assayed with DA as the substrate: the higher the DOPAL accumulation, the greater the ethanol intake suppression.

EXAMPLE VIII

Antidipsotropic Index as a Measure of Ethanol Intake Suppression

Figure 3:
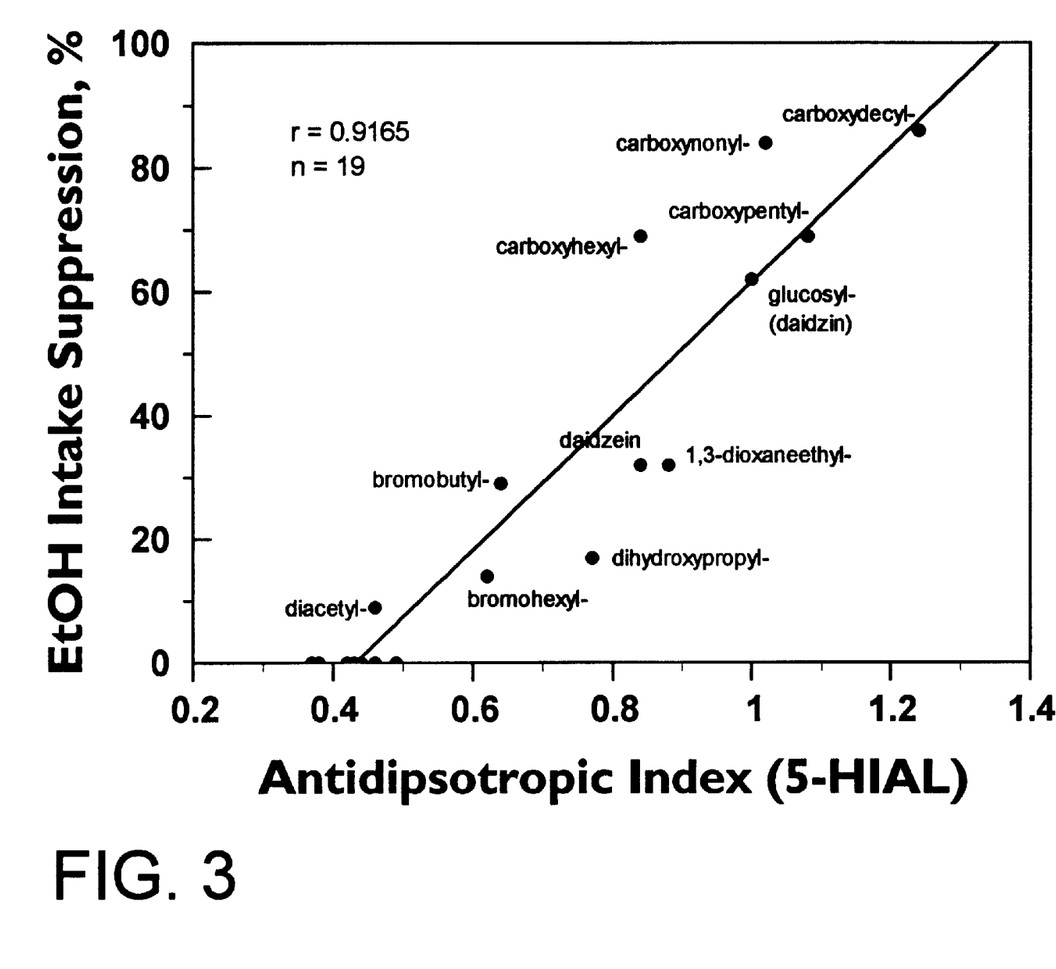
FIG. 3 is a graph of the percent ethanol intake suppression versus antidipsotropic index which is the ratio of 5-HIAL accumulation for a daidzin analog and 5-HIAL accumulation for daidzin.

According to the teachings of the present invention, an assay based upon the enzyme systems of serotonin or dopamine is described. Candidate compounds were screened for their antidipsotropic properties by determining their ability to interfere, inhibit or otherwise interact with the enzyme systems of serotonin or dopamine in a manner to alter the amount of aldehyde present in the enzyme system. The candidate compounds screened according to the assay of the present invention were those identified in the preceding Example. The 5-HIAL accumulation, % control was determined for each compound and then normalized to the 5-HIAL accumulation, % control of daidzin to produce an antidipsotropic index (5-HIAL) of the present invention. A similar antidipsotropic index can be created based upon the DOPAL accumulation, % control indicated in FIG. 2. The antidipsotropic index for each compound was then plotted as a function of ethanol suppression previously determined for each compound. The results shown in FIG. 3 indicate a direct linear correlation between the antidipsotropic index and ethanol intake suppression, i.e., the greater the antidipsotropic index for the compound, the greater the ethanol intake suppression capability of the compound, providing for the first time a mechanistic basis and reliable index based upon aldehyde intermediates of monoamine metabolism useful as a rapid in vitro assay that could eventually be automated for high throughput drug screening by conventional means known to those skilled in the in vitro assay art.

For instance, the aldehyde intermediates accumulated during the mitochondria-catalyzed monoamine metabolism described in Example VI can be measured be a bioluminescent assay using bacterial luciferase. Unlike the HPLC method, the bioluminescent assay is simple and can easily be automated for high throughput drug screening. Bacterial luciferase catalyzes the oxidation of $FMNH_2$ and a long chain aldehyde (e.g., n-decylaldehyde), a reaction which also results in light emission. Bacterial luciferase is used to determine substrate/binding activity with 5-HIAL or DOPAL. Alternatively, the mitochondrial assay described in Example VI is modified by using a long chain primary amine, instead of 5-HT or DA, as the substrate, to accommodate the substrate requirement of bacterial luciferase. Monoamine oxidase has been shown to catalyze the conversion of long chain primary amines (e.g., n-decylamine) to their corresponding aldehydes (n-decylaldehyde).

It is to be understood that the embodiments of the present invention which have been described are merely illustrative of some of the applications of the principles of the invention. Numerous modifications may be made by those skilled in the art based upon the teachings presented herein without departing from the true spirit and scope of the invention.

What is claimed is:

1. A method for identifying compounds effective in reducing alcohol consumption comprising selecting a test compound,     establishing an enzyme system including a substrate of monoamine oxidase,     allowing catalytic oxidative deamination of a substrate of monoamine oxidase into aldehyde,     allowing catabolism of aldehyde into carboxylic acid by ALDH-2,     measuring a first concentration of aldehyde,     contacting the test compound with the enzyme system,     measuring a second concentration of aldehyde,     comparing the first concentration to the second concentration.

2. The method of claim 1 wherein the substrate of monoamine oxidase is serotonin or dopamine.

3. The method of claim 1 wherein the aldehyde is 5-hydroxyindole-3-acetic acid or 3,4-dihydroxyphenylacetic acid.

4. A method for identifying compounds effective in reducing alcohol consumption comprising selecting a test compound,     establishing an enzyme system including a substrate of monoamine oxidase,     allowing catalytic oxidative deamination of a substrate of monoamine oxidase into aldehyde,     allowing catabolism of aldehyde into carboxylic acid by ALDH-2,     measuring a first concentration of aldehyde,     contacting the test compound with the enzyme system,     measuring a concentration of aldehyde, and     comparing the concentration of aldehyde with concentrations of aldehyde produced by compounds having known antidipsotropic activity.

5. The method of claim 4 wherein the substrate of monoamine oxidase is serotonin or dopamine.

6. The method of claim 4 wherein the aldehyde is 5-hydroxyindole-3-acetic acid or 3,4-dihydroxyphenylacetic acid.

* * * * *

UNITED STATES PATENT AND TRADEMARK OFFICE
CERTIFICATE OF CORRECTION

PATENT NO.    : 6,121,010
DATED         : September 19, 2000
INVENTOR(S)   : Bert-Vallee and Wing-Ming Keung It is certified that error appears in the above-identified patent and that said Letters Patent is hereby corrected as shown below:

Column 14,
Lines 14-16, kindly amend the claim as follows:
-- 3. The method of claim 1 wherein the aldehyde is "5-hydroxyindole-3-acetic acid" -- 5-hydroxyindole-3-acetaldehyde -- or "3,4-dihydroxyphenylacetic acid" -- 3,4-dihydroxyphenyl-3-acetaldehyde --.

Lines 37-39, kindly amend the claim as follows:
-- 6. The method of claim 4 wherein the aldehyde is "5-hydroxyindole-3-acetic acid" -- 5-hydroxyindole-3-acetaldehyde -- or "3,4-dihydroxyphenylacetic acid" -- 3,4-dihydroxyphenyl-3-acetaldehyde --.

Signed and Sealed this

Seventh Day of October, 2003

JAMES E. ROGAN
*Director of the United States Patent and Trademark Office*